US011395827B2

(12) United States Patent
Hansson et al.

(10) Patent No.: US 11,395,827 B2
(45) Date of Patent: *Jul. 26, 2022

(54) OIL-IN-WATER EMULSION OF MOMETASONE AND PROPYLENE GLYCOL

(71) Applicant: GALENICA AB, Malmo (SE)

(72) Inventors: Henri Hansson, Helsingborg (SE); Anna Karin Morén, Malmö (SE)

(73) Assignee: GALENICA AB, Malmo (SE)

( * ) Notice: Subject to any disclaimer, the term of this patent is extended or adjusted under 35 U.S.C. 154(b) by 14 days.

This patent is subject to a terminal disclaimer.

(21) Appl. No.: 14/187,997

(22) Filed: Feb. 24, 2014

(65) Prior Publication Data

US 2014/0242171 A1   Aug. 28, 2014

Related U.S. Application Data

(63) Continuation of application No. 13/319,758, filed as application No. PCT/EP2010/002921 on May 12, 2010, now Pat. No. 8,728,497.

(30) Foreign Application Priority Data

May 12, 2009   (DK) .......................... PA 200900601

(51) Int. Cl.
*A61K 9/107*   (2006.01)
*A61K 31/58*   (2006.01)
*A61K 47/10*   (2017.01)
*A61K 9/00*   (2006.01)

(52) U.S. Cl.
CPC ............ *A61K 31/58* (2013.01); *A61K 9/0014* (2013.01); *A61K 9/107* (2013.01); *A61K 47/10* (2013.01)

(58) Field of Classification Search
None
See application file for complete search history.

(56) References Cited

U.S. PATENT DOCUMENTS

| 4,282,216 A | 8/1981 | Rovee et al. |
| 4,808,610 A | 2/1989 | Munayyer et al. |
| 5,696,105 A | 12/1997 | Hackler |
| 5,874,074 A | 2/1999 | Smith |

(Continued)

FOREIGN PATENT DOCUMENTS

| EP | 1 886 686 | 2/2008 |
| WO | WO 91/08733 A1 | 6/1991 |

(Continued)

OTHER PUBLICATIONS

Barry, Brian W. "Mode of action of penetration enhancers in human skin." Journal of Controlled Release 6.1 (1987): 85-97.*

(Continued)

*Primary Examiner* — Nissa M Westerberg
(74) *Attorney, Agent, or Firm* — Foley & Lardner LLP (57) ABSTRACT

Novel pharmaceutical compositions of mometasone or a pharmaceutically acceptable derivate thereof in the form of an oil-in-water emulsion, notably a cream. The composition has excellent stability and therapeutic effect. The compositions contain mometasone in micronised form, propylene glycol and water and the weight ratio between the propylene glycol and water contained in the oil-in-water emulsion is from 1:1 to about 1:3.

22 Claims, 6 Drawing Sheets

(56) References Cited

U.S. PATENT DOCUMENTS

| | | | |
|---|---|---|---|
| 5,952,003 A * | 9/1999 | Guentensberger ... | A61K 9/4858 424/451 |
| 6,075,056 A | 6/2000 | Quigley, Jr. et al. | |
| 6,127,353 A | 10/2000 | Yuen et al. | |
| 2002/0107265 A1* | 8/2002 | Chen .................... | A61K 9/1075 514/310 |
| 2004/0248866 A1 | 12/2004 | Moldenhauer | |
| 2005/0196462 A1* | 9/2005 | Alimi .................... | A61L 2/0088 424/600 |
| 2005/0220823 A1 | 10/2005 | Saunier et al. | |
| 2006/0034798 A1 | 2/2006 | Mosbey et al. | |
| 2006/0104968 A1* | 5/2006 | Bookbinder ............ | A61P 25/00 424/94.61 |
| 2007/0020213 A1 | 1/2007 | Tamarkin et al. | |
| 2007/0099883 A1 | 5/2007 | Calis et al. | |
| 2008/0066744 A1 | 3/2008 | Chaudhry et al. | |
| 2012/0128736 A1 | 5/2012 | Hansson et al. | |
| 2012/0171252 A1 | 7/2012 | Hansson et al. | |
| 2018/0228723 A1 | 8/2018 | Hansson et al. | |

FOREIGN PATENT DOCUMENTS

| | | |
|---|---|---|
| WO | WO 03/097070 | 11/2003 |
| WO | WO 03/097070 A1 | 11/2003 |
| WO | WO 2004/105686 A2 | 12/2004 |
| WO | WO 2008/126076 | 10/2008 |
| WO | WO 2008/126076 A2 | 10/2008 |

OTHER PUBLICATIONS

Arellano, A., et al. "Influence of propylene glycol and isopropyl myristate on the in vitro percutaneous penetration of diclofenac sodium from carbopol gels."0 European journal of pharmaceutical sciences 7.2 (1999): 129-135.*
Food and Drug Administration, "Guidance for industry. Topical dermatologic corticosteroids: in vitro bioequivalence." Center for Drug Evaluation and Research, Rockville, MD (1995).*
Food and Drug Administration. "Guidance for industry: bioavailability and bioequivalence studies for orally administered drug products—general considerations." Food and Drug Administration (2000).*
"What does topical application mean?" from https://www.definitions.net/print.php?term=topical+medication, accessed Nov. 26, 2019 (Year: 2019).*
U.S. Appl. No. 15,890,610, filed Feb. 7, 2018, Henri et al.
PTAB Decision on Appeal dated Dec. 8, 2017 in U.S. Appl. No. 13/319,760.
ELOCON, Cream 0.1% (data sheet dated Jul. 17, 2002).
Chang et al., "Generic Development of Topical Dermatologic Products: Formulation Development, Process Development, and Testing of Topical Dermatologic Products," The AAPS Journal, vol. 15, No. 1, pp. 41-52 (Jan. 2013).
Oakley, "Topical corticosteroid treatment for skin conditions," BPJ, Issue 23, 6 pages, (Sep. 2009).
Office Action dated Jul. 11, 2019 in U.S. Appl. No. 15/890,610.
Office Action dated May 19, 2020 in U.S. Appl. No. 15/890,610.
Barel et al., Handbook of Cosmetic Science and Technology, pp. 151-155 (Marcel Dekker Inc., 2001).
Desai et al., "Topical and Transdermal Delivery Systems," in Gibaldi'S Drug Delivery Systems in Pharmaceutical Care, (Desai and Lee, eds.) (Am. Soc. Health-System Pharmacists, 2007).
Eur. Pharmacopoeia, 10.0, vol. 1, p. 936 (10th ed. 2020).
Feldmann et al., "Penetration of $^{14}C$ Hydrocortisone Through Normal Skin," Arch Dermatol, 91: 661-66 (Jun. 1965).
Fini et al., "Control of Transdermal Permeation of Hydrocortisone Acetate from Hydrophilic and Lipophilic Formulations," AAPS PharmSciTech, 9(3): 762-68, (Sep. 2008) (Published online Jun. 18, 2008).
Jacob et al., "Corticosteroid classes: A quick reference guide including patch test substances and cross-reactivity," J. Am. Acad. Derm. 54: 723-27 (2006).
Laba, "How Do I Thicken My Cosmetic Formula?" Cosmetic & Toiletries Magazine, 116(11): 35-44 (Nov. 2001).
Leiferman et al., "Characterization of the Glucocorticoid Receptor in Human Skin," J. Invest. Derm., 81(4): 355-360 (1983).
Mometasone Furoate DB14512, Available online https://www.drugbank.ca/drugs/DB14512, at p. 7 (created Jul. 2018, updated Mar. 2020).
Mundstock et al., "Alteration of the Structure of Human Stratum Corneum Facilitates Transdermal Delivery," Open Derm. J., 8: 72-79 (2014).
Mustapha et al., "Influence of drug concentration on the diffusion parameters of caffeine," Indian J Pharmacol., 43(2): 157-162 (Apr. 2011).
Office Action dated Dec. 19, 2019, in U.S. Appl. No. 15/890,610.
Office Action dated Nov. 20, 2020 in U.S. Appl. No. 15/890,610.
Office Action dated Feb. 13, 2013 in U.S. Appl. No. 13/319,760.
Office Action dated Dec. 11, 2013 in U.S. Appl. No. 13/319,760.
Office Action dated Mar. 25, 2014 in U.S. Appl. No. 13/319,760.
International Search Report dated Aug. 11, 2010 in application No. PCT/EP2010/002921.
Prakash et al., "Topical mometasone. A review of its pharmacological properties and therapeutic use in the treatment of dermatological disorders," Drugs, vol. 55, No. 1, pp. 145-163, Jan. 1, 1998.
ICI Americas Inc., "The HLB System—a time-saving guide to emulsifier selction," edited and reprinted from Chemmunique, revised 1980.
Sznitowska et al., "Submicron emulsions as drug carriers—Studies on destabilization potential of various drugs," European Journal of Pharmaceutical Sciences, vol. 12, pp. 175-179, 2001.
Woodford et al., "The placebo response to white soft paraffin propylene glycol in the skin blanching test," British Journal of Dermatology, vol. 89, pp. 53-59, 1973.
Office Action dated Apr. 1, 2013 in U.S. Appl. No. 13/319,758.
Office Action dated Oct. 30, 2013 in U.S. Appl. No. 13/319,758.
Notice of Allowance dated Jan. 9, 2014 in U.S. Appl. No. 13/319,758.

* cited by examiner

OIL-IN-WATER EMULSION OF MOMETASONE AND PROPYLENE GLYCOL

FIELD OF THE INVENTION

The present invention provides a novel pharmaceutical composition of mometasone or a pharmaceutically acceptable derivate thereof in the form of an oil-in-water emulsion, notably a cream. The composition has excellent stability and therapeutic effect.

BACKGROUND OF THE INVENTION

The exceptionally poor solubility of mometasone furoate has delayed the development of efficacious, economic and cosmetically elegant topical formulation. The existing mometasone creams on the market today are all based on water-in-oil emulsions.

One of the most challenging tasks for formulators is to incorporate poorly water-soluble drugs into effective products. Improving the solubility of the lipophilic drugs is considered to improve the bioavailability of the product. Therefore, formulations where the active substance is in a dissolved state are generally preferred. Normally the active substance is in a solubilized form when permeating the skin. Therefore it is also generally considered as an advantage when the active substance is in a solubilized form in the topical formulation in order to obtain a suitable therapeutic response.

BACKGROUND OF THE INVENTION

U.S. Pat. No. 4,808,610 (Schering Corp) and U.S. Pat. No. 7,312,207 (Taro Pharmaceuticals) relate to mometasone containing compositions for topical use, wherein the composition is in the form of a water-in-oil (w/o) emulsion.

WO 91/08733 (Schering Corp) relates to an oil-in-water (o/w) emulsion comprising a lipophilic active drug substance (e.g. mometasone). The examples show the necessity of using N-methyl-2-pyrrolidone in order to enhance the vasoconstrictor effect. In the examples propylene glycol is used in a concentration of 10% w/w.

WO 2008/126076 (Perrigo Israel Pharmaceuticals Ltd.) relates to a low-dose mometasone formulation. Exemplary formulations are creams containing 0.075% mometasone, a polyol, a gelling agent an oily phase, and water. A low-dose mometasone formulation is desired in order to reduce the toxicity of a mometasone formulation. It is believed that a formulation of WO 2008/126076 has a relatively low systemic steroid absorption. No in vivo studies are reported.

DETAILED DESCRIPTION OF THE INVENTION

The present invention provides an oil-in-water emulsion (o/w) containing mometasone as an active drug substance. Moreover, the emulsion contains propylene glycol, i.e. 1,2-propane-diol.

As it appears from the examples herein, an o/w emulsion of the present invention provides a bioavailability and a therapeutic effect of mometasone that is comparable to the marketed w/o emulsion (Elocon® cream). LEach gram of Elocon® Cream 0.1% contains mometasone furoate, USP (1 mg) in a cream base of hexylene glycol, NF; phosphoric acid, NF; propylene glycol stearate (55% monoester); stearyl alcohol and ceteareth-20; titanium dioxide, USP; aluminum starch octenylsuccinate (Gamma Irradiated); white wax, NF; white petrolatum, USP; and purified water, USP.) As briefly discussed in the introduction, the general view has been that in order to achieve a suitable therapeutic response it is of utmost importance to have the active drug dissolved or solubilised in the composition. Considering the lipid nature of mometasone furoate it has thus, until now, been considered to have mometasone furoate dissolved in the formulation. However, as discussed below, the present inventors have found that it is not necessary to have all mometasone dissolved in an o/w emulsion in order to achieve a suitable therapeutic effect.

The present inventors have found that using mometasone (e.g. mometasone furoate) and propylene glycol in a relatively high concentration (from 20% to 45% w/w) enables the formulation of an o/w emulsion, wherein mometasone is at least partly dissolved in the formulation (as appears from the examples herein, mometasone furoate is partly dissolved in the formulation). Moreover, it is possible to obtain an o/w emulsion with a similar therapeutic effect to that seen with Elocon® cream, i.e. the o/w emulsion only need to be applied once daily. To this end and as supported by the results reported herein, a suitable weight ratio between propylene glycol and water in the o/w emulsion seems to be important for the once daily administration. It seems as if a too large or a too low ratio will not result in the desired effect and/or the desired bioavailability. Another factor that seems to be of importance is the presence of mometasone (e.g. mometasone furoate) in micronised form. Normally, mometasone is not dissolved (or only partly dissolved) in a composition of the invention. The results reported herein indicate the importance of having undissolved mometasone in micronised from. Thus, in general, 100% of the mometasone particles have a particle size of at the most 20 µm, 99% has a particle size of at the most 15 µm, and 80% has a particle size of at the most 5 µm when measured by means of a laser scattering method. When determining the particle size by means of light microscopy (which is the method preferred, when the particle size is measured in the final composition), no particle of mometasone should exceed 40 µm. Most particles (more than 80% and visually evaluated in the microscope) have a size between 10 and 20 µm. Eventual particle growth over time in the composition should not result in any particles exceeding 50 µm, when measured with light microscopy. Other factors may also influence the results such as the nature of the other ingredients employed. However, the two most important factors in compositions of the present invention seem to be the weight ratio and particle size as discussed above. A suitable weight ratio between propylene glycol and water is from about 1:1 to about 1:3. As illustrated in the examples, it is possible to obtain an emulsion with balanced content of mometasone (e.g. mometasone furoate), propylene glycol and water that is bioequivalent with the w/o Elocon® cream.

An oil-in-water emulsion as described herein may have a therapeutic effect similar or better to that of ELOCON® 0.1% cream, as determined as described in Example 2 herein. As used herein, "similar or better therapeutic effect" compared to that of ELOCON® 0.1% cream means that the mean AUC (area under the curve showing the blanching index as a function of time) for the oil-in-water emulsion is 85% or more such as 90% or more compared to the AUC of ELOCON® 0.1% cream, as determined as described in Example 2 herein.

A composition of the invention contains two phases, an aqueous phase, which is the continuous phase and an oil phase, which is the dispersed phase that is homogeneously distributed in the continuous phase (i.e. as generally seen in o/w emulsions). Moreover, the active drug substance, mometasone (e.g. mometasone furoate), is partly dissolved and partly present in the form of fine particles, notably in micronized form.

More specifically, the present invention provides an oil-in-water emulsion comprising mometasone (M) or a pharmaceutically acceptable derivative thereof and propylene glycol of a concentration from 15 to about 45% w/w such as from 20% w/w to about 45% w/w, from about 20% w/w to 40% w/w, from 15% w/w to 30% w/w or from 20% to 30% w/w. The use of propylene glycol in o/w emulsions of mometasone is illustrated in the Examples herein. It is contemplated that other alkane-diols as well may be used in combination with propylene glycol, such as propylene glycol (1,2-propane-diol), butylene glycol (1,3-butane-diol), pentylene glycol (1,5-pentane-diol), and/or hexylene glycol (1-methyl-2,4-pentane-diol). When butylene glycol, pentylene glycol or hexylene glycol is used in combination with propylene glycol the concentration of such diols may be from about 1% w/w to about 20% w/w (notably from about 5% w/w to about 20% w/w).

As evident from the examples herein, incorporation of propylene glycol is very important in order to obtain the desired effect, and not only is it the incorporation of propylene glycol in the emulsion, but also the concentration of propylene glycol, either expressed as the concentration in the total emulsion, or, more specific, expressed as a weight ratio between propylene glycol and water. When an oil-in-water emulsion of the invention is applied to the skin, the water in the composition is subject to evaporation. Thus, not only the weight ratio between propylene glycol and water in the composition may be important, but also the ratio between propylene glycol and mometasone or a pharmaceutically acceptable derivative thereof may have impact on the therapeutic result. One or more of these factors are contemplated to be important for whether an emulsion can be obtained with suitable properties with respect to therapeutic effect.

In the present context, the term "mometasone" includes mometasone or pharmaceutically acceptable derivatives thereof. Thus, the term includes mometasone as such as well as suitable ester derivatives such as esters with organic acid normally used in pharmaceutics including the furoate ester. Moreover, "mometasone or pharmaceutically acceptable derivatives thereof" includes any form such as anhydrous form, hydrate forms including the monohydrate, solvates other than hydrates etc., as well as amorphous, polymorph and crystalline forms thereof. In the present context, all calculation relating to "mometasone or pharmaceutically acceptable derivatives thereof" is based on mometasone furoate. Accordingly, if another derivative is employed, an equivalent amount of mometasone furoate must be calculated based on the molecular weights of the derivative and the mometasone furoate.

The concentration of mometasone (calculated as mometasone furoate) in an emulsion of the present invention may be from about 0.01% to 2% w/w, normally from 0.05% to 0.2% w/w, from 0.075% to 0.2% w/w such as about 0.1% w/w.

In an emulsion according to the invention, mometasone (mometasone furoate) is not fully dissolved. Accordingly, a part of mometasone or a pharmaceutically acceptable derivative thereof is present in undissolved form, typically from about 25% to about 35% w/w of the total amount of mometasone present in the emulsion. In order to improve the dispersibility of the undissolved mometasone as well as the absorption rate, mometasone should be employed in micronised form. As it appears from the examples herein, mometasone, e.g. mometasone furoate, should be employed in micronised form, wherein 100% has a particle size of at the most 20 μm, 99% has a particle size of at the most 15 μm, and 80% has a particle size of at most 5 μm (when determined by laser microscopy). It is contemplated that during the manufacturing process, as described herein, mometasone furoate may partly dissolve, but it is not fully dissolved. This seems to be of importance in order to control the particle size in the final composition. If mometasone is fully dissolved during the manufacturing method, a risk will occur that the mometasone that precipitates in the composition has a too large particle size. Accordingly, it is envisaged that the mean particle size (and/or particle size distribution) of mometasone furoate employed is important in order to obtain reproducible therapeutic results.

As mentioned above, other diols may be used in combination with propylene glycol. Such diols include butylene glycol, pentylene glycol or hexylene glycol. Specific examples include butane-1,3-diol, pentane-1,5-diol and 1-methyl-2,4-pentadiol. It is envisaged that other diols also may be suitable for use in the present context provided that it is suitable and safe for topical use.

As mentioned above, the concentration of propylene glycol in an emulsion of the invention is from about 20% to about 45% w/w. In general, the concentration of propylene glycol is from about 20% to about 40% w/w such as from about 20% to about 30% w/w.

As mentioned above, the weight ratio between propylene glycol and water seems to be important in order to achieve the desired therapeutic effect. Moreover, the weight ratio between propylene glycol and mometasone (M) may also be a useful parameter to decide the amount of alkane-diol in an emulsion of the invention. In the following table calculations of suitable ranges of the ratio are given. As seen from the table, the lower limit is normally not less than 10, such as in a range of from 10 to 100 and the upper limit is normally 4500 or less such as in a range of from 600 to 4500. Normally, the ratio is 100 or more such as from 100 to 900 or from about 200 to about 450, and M is calculated as mometasone furoate. Specifically, the weight ratio between propylene glycol and mometasone (M) is from 200 to 300, such as 200, 225, 250, 275 or 300, and M is calculated as mometasone furoate.

| Propylene glycol % w/w I | Mometasone (calculated as furoate) % w/w II | Ratio I/II |
| --- | --- | --- |
| 20-45 | 0.01-2 | 10-4500 |
| 20-40 | 0.01-2 | 10-4000 |
| 20-30 | 0.01-2 | 10-3000 |
| 20-45 | 0.05-1 | 20-900 |
| 20-40 | 0.05-1 | 20-800 |
| 20-30 | 0.05-1 | 20-600 |
| 20-45 | 0.05-0.5 | 40-900 |
| 20-40 | 0.05-0.5 | 40-800 |
| 20-30 | 0.05-0.5 | 40-600 |
| 20-45 | 0.05-0.2 | 100-900 |
| 20-40 | 0.05-0.2 | 100-800 |
| 20-30 | 0.05-0.2 | 100-600 |

Generally, the weight ratio between propylene glycol and mometasone (M) is 100 or more such as, e.g. 100 or more or 200 or more, such as, e.g., from 100 to 900, from about 200 to about 500, and M is calculated as mometasone furoate.

Specifically, the weight ratio between propylene glycol and mometasone (M) is from 200 to 450, from 200 to 400, and M is calculated as mometasone furoate.

In particular, the weight ratio between propylene glycol and mometasone (M) is from 200 to 300, such as 200, 225, 250, 275 or 300, and M is calculated as mometasone furoate.

Moreover, the weight ratio between propylene glycol and water (PG:W) is indicative of whether a suitable emulsion is obtained (with respect to therapeutic activity). Thus, the weight ratio is normally from 1:1 to about 1:3 such as from about 1:1.5 to about 1:2.5 or from 1:1.75 to 1:2.25. In the examples a suitable ratio is found to be about 1:2 or 1:2.1 when 25% propylene glycol is employed and from about 1:2.8 to 1:2.9 when 20% propylene glycol is employed.

In the literature, combinations of steroids with other active ingredients are described. However, as is evident from the examples herein, the invention is directed to an oil-in-water emulsion, wherein mometasone or a pharmaceutically acceptable derivative thereof is the sole therapeutically active ingredient. Further active ingredients may be added provided that the bioavailability and therapeutic effect of mometasone are not negatively affected. Moreover, further active ingredients may not have any negative effect on the stability of the o/w emulsion.

As mentioned above, an emulsion is established by mixing an aqueous phase and an oil phase. In an oil-in-water emulsion, the oil is present in droplets homogeneously dispersed in the aqueous phase. In order to stabilize the emulsion against phase separation, surface active agents or emulsifying agents are added.

In an emulsion of the present invention, the oil phase comprises an oil selected from a group consisting of vegetable oils and fats, animal oils and fats, mineral oils, ester oils, silicon oils or waxes. Notably, the oil/fat is a vegetable oil/fat such as coconut oil, olive oil, sunflower oil and canola oil etc. Fats can be defined as bulk storage material produced by plants, animals and microorganisms that contain aliphatic moieties, such as fatty acid derivatives. These are mainly, but not entirely, mixtures of triglycerols (triglycerides) and are known as oils or fats depending on whether they are liquid or solid at room temperature. In the present context, the term "oil" also includes "fat" and oil/fat may also be produced synthetically or semi-synthetically.

The concentration of the oil/fat in the emulsion is from about 3 to about 30% w/w, notably from about 5 to about 15% w/w.

As mentioned above, stabilization of an oil-in-water emulsion according to the invention may suitably be carried out by adding one or more emulsifying agents. An emulsion of the present invention may therefore comprise one or more emulsifying agents. As seen from the examples herein use of three emulsifying agents having a HLB (hydrophilic-lipophilic balance) in the range 3-20, one with a high HLB, i.e. a HLB of, from about 11-20 and two with a low HLB, i.e. a HLB of, from about 3-11, gives the desired result with respect to stability without compromising the therapeutic effect.

Suitable emulsifying agents for use in a composition of the invention may be selected from the group consisting of glycerol alkyl esters, macrogol alkyl esters, polyoxyethyleneglycol alkyl esters, fatty acids, polyoxyethylene sorbitan esters, polyoxyethylene alkyl ethers, galactolipids.

Specific emulsifying agents for use in a composition of the invention are glycerol monostearate 40-55, macrogol stearate, and stearic acid.

The concentration of each emulsifier when present in an emulsion according to the present invention ranges from 1-5% w/w.

Moreover, an oil-in-water emulsion according to the invention may comprise a viscosity-increasing agent. Viscosity-increasing agents suitable for use in an emulsion may be selected from the group consisting of fatty alcohols (concentration range: 5-15% of total emulsion) However, the concentration normally dependents on the specific type of fatty alcohol used and a person skilled in the art will know how to adjust the concentration of such specific concentrations to obtain the desired viscosity.

As seen from the examples herein, a suitable viscosity-increasing agent is cetostearyl alcohol.

In general, the concentration of the viscosity-increasing agent in the form of a fatty alcohol ranges from 5% to 15% w/w.

An emulsion of the invention is intended for topical use, i.e. as a cream to apply on the skin. Accordingly, pH may be adjusted to a skin-friendly value taking into consideration stability issues relating to mometasone. A suitable pH is below 6 such as from about 3 to about 6 or from about 4.0 to about 5.0. pH may be adjusted by use of one or more pH adjusting agent, which is selected from the group consisting of hydrochloric acid, phosphoric acid, sodium hydroxide, citrate buffer, phosphate buffer, phthalate buffers, acetate buffers, succinate buffers. In order to arrive at a pH below 6 or about 4.0-5.0, a citrate buffer has proved to be suitable.

Moreover, an emulsion of the present invention may contain one or more fragrances. Addition of a preservative agent is normally not required as propylene glycol itself has antimicrobial effect when it is added in a sufficient concentration.

More specifically, the invention relates to an oil-in-water emulsion having one of the following compositions:

| Ingredient | Emulsion A | Variation A.1 | Variation A.2 | Variation A.3 |
|---|---|---|---|---|
| Active ingredient | Mometasone furoate | 0.05% w/w | 0.1% w/w | 0.2% w/w |
| $C_3$ alkane diol Chemical name | Propylene glycol 1,2-propanediol | 20% w/w | 20% w/w | 20% w/w |
| Oil | Vegetable oil | 5-25% w/w, notably 5-15% w/w | 5-25% w/w, notably 5-15% w/w | 5-25% w/w, notably 5-15% w/w |
| Emulsifying agents | | 1-15% w/w | 1-15% w/w | 1-15% w/w |
| Viscosity-increasing agent$^a$ | | | | |

-continued

| Ingredient | Emulsion A | | | |
|---|---|---|---|---|
| pH adjusting agent | | 0.1-1% w/w | 0.1-1% w/w | 0.1-1% w/w |
| Water | | Up to 100% w/w | Up to 100% w/w | Up to 100% w/w |

| Ingredient | Emulsion A | Variation A.4 | Variation A.5 | Variation A.6 |
|---|---|---|---|---|
| Active ingredient | Mometasone furoate | 0.05% w/w | 0.1% w/w | 0.2% w/w |
| C$_3$ alkane diol | Propylene glycol | 25% w/w | 25% w/w | 25% w/w |
| Chemical name | 1,2-propanediol | | | |
| Oil | Vegetable oil | 5-25% w/w, notably 5-15% w/w | 5-25% w/w, notably 5-15% w/w | 5-25% w/w, notably 5-15% w/w |
| Emulsifying agents | | 1-15% w/w | 1-15% w/w | 1-15% w/w |
| Viscosity-increasing agent$^a$ | | | | |
| pH adjusting agent | | 0.1-1% w/w | 0.1-1% w/w | 0.1-1% w/w |
| Water | | Up to 100% w/w | Up to 100% w/w | Up to 100% w/w |

| Ingredient | Emulsion A | Variation A.7 | Variation A.8 | Variation A.9 |
|---|---|---|---|---|
| Active ingredient | Mometasone furoate | 0.05% w/w | 0.1% w/w | 0.2% w/w |
| C$_3$ alkane diol | Propylene glycol | 30% w/w | 30% w/w | 30% w/w |
| Chemical name | 1,2-propanediol | | | |
| Oil | Vegetable oil | 5-25% w/w, notably 5-15% w/w | 5-25% w/w, notably 5-15% w/w | 5-25% w/w, notably 5-15% w/w |
| Emulsifying agents | | 1-15% w/w | 1-15% w/w | 1-15% w/w |
| Viscosity-increasing agent$^a$ | | | | |
| pH adjusting agent | | 0.1-1% w/w | 0.1-1% w/w | 0.1-1% w/w |
| Water | | Up to 100% w/w | Up to 100% w/w | Up to 100% w/w |

$^a$the concentration of the viscosity-increasing agent, if present, depends on the nature of the agent, cf. the text above Further examples are:

An oil-in-water emulsion according to the invention containing:

0.05-0.2% w/w of mometasone or a pharmaceutically acceptable derivative thereof (calculated as mometasone furoate)

20-45% w/w of propylene glycol, 3-30% w/w of a vegetable oil/fat, 1-15 w/w of one or more emulsifying agents, optionally 0.1-1% w/w of a pH adjusting agent, optionally 5-15% w/w of a viscosity increasing agent, up to 100% w/w of water.

An oil-in-water emulsion according to the invention containing:

0.06-0.15% w/w of mometasone or a pharmaceutically acceptable derivative thereof (calculated as mometasone furoate)

20-40% w/w of propylene glycol, 5-15% w/w of a vegetable oil/fat, 1-10% w/w of one or more emulsifying agents, 0.1-1% w/w of a pH adjusting agent to adjust pH of the emulsion to about 4-6, optionally 5-15% w/w of a viscosity increasing agent, up to 100% w/w of water.

An oil-in-water emulsion according to the invention containing:

0.1% w/w of mometasone or a pharmaceutically acceptable derivative thereof (calculated as mometasone furoate)

from 20 to 30% w/w of propylene glycol, from 5 to 10% w/w of a vegetable oil/fat, from 5-10% w/w of one or more emulsifying agents, 0.1-1% w/w of a pH adjusting agent to adjust pH of the emulsion to about 4-6, 5-10% w/w of a viscosity increasing agent, up to 100% w/w of water.

Notably, an oil-in-water emulsion according to the invention does not contain N-methyl-2-pyrrolidone.

The present invention also provides a method for manufacturing of an oil-in-water emulsion of the invention. The procedure is detailed described in Example 1 and a person skilled in the art will understand that the individual ingredients mentioned can be replaced by the ingredients mentioned in Table 1 below having the same functionality and in the concentration ranges mentioned. More specifically, the method comprises i) preparing the oil phase by mixing the ingredients that make up the oil phase and heating to a temperature of from 60° C. to 80° C., notably from 65° C. to 75° C. such as about 70° C., ii) preparing the aqueous phase by a) preparing a dispersion of mometasone or a pharmaceutically acceptable derivative thereof such as mometasone furoate in part of the aqueous phase, b) preparing the remaining part of the aqueous phase by dissolving the ingredients, optionally by heating to 55° C. to 75° C., notably from 60° C. to 70° C. such as about 65° C., and c) addition of the dispersion resulting from a) to the remaining part of the aqueous phase resulting from b) to obtain the aqueous phase, iii) transferring the oil phase i) to the aqueous phase ii) or optionally ii) to i)

iv) mixing until an emulsion is obtained, v) optionally, subjecting the thus obtained emulsion to vacuum conditions, vi) optionally, homogenizing the emulsion optionally under vacuum conditions, vii) optionally, addition of one or more fragrance agents, viii) cooling the thus obtained emulsion.

The ingredients, included in the oil phase i) above, are typically an oil as described herein and all the ingredients that are soluble in the oil phase (apart from mometasone). Such ingredients may be one or more emulsifying agents, one or more viscosity-increasing agents, one or more preservatives, if present, optionally one or more fragrance agents or the like. The ingredients included in the aqueous phase is—apart from mometasone—water and ingredients that are soluble in water such as e.g. propylene glycol and, optionally one or more $C_3$-$C_6$ alkane-diols, one or more pH regulating agents, if present, one or more water-soluble viscosity-increasing agents, if present, one or more fragrance agents, if present, one or more preservatives, if present, and the like.

The invention is further illustrated in the following Figures and Examples without limiting the invention thereto.

The invention is further illustrated in the following non-limiting examples.

EXAMPLES

Example 1

Complete Composition

The complete composition of the 0.1% mometasone furoate oil-in-water cream is given in table 1.

TABLE 1

Complete composition of 0.1% mometasone furoate oil-in-water cream.

| Name of ingredient | Quantity (mg/g) | Function | Concentration range (mg/g) | Replacement |
|---|---|---|---|---|
| Active substance | | | | |
| Mometasone furoate, micronized 100% ≤20 μm 99% ≤15 μm 80% ≤5 μm | 1.0 | Drug substance | 0.10-2.0 | — |
| Excipients | | | | |
| Coconut oil | 80 | Emollient | 30-300 | Vegetable oil/fat, animal oil/fat, mineral oil, ester oil or wax, silicon oil |
| Stearic acid | 20 | Emulsifying agent | 10-50 | glycerol alkyl esters, macrogol alkyl esters, polyoxyethyleneglycol alkyl esters, fatty acids, polyoxyethylene sorbitan esters, polyoxyethylene alkyl ethers, galactolipids |
| Macrogol Stearate | 30 | Emulsifying agent Solubilizer of drug substance | 10-50 | |
| Glycerol monostearate 40-55 | 30 | Emulsifying agent | 10-50 | |
| Cetostearyl alcohol | 70 | Viscosity-increasing agent | 50-150 | Fatty alcohols |
| Propylene glycol | 250 | Solvent Solubilizer of drug substance | 200-450 | |

TABLE 1-continued

Complete composition of 0.1% mometasone furoate oil-in-water cream.

| Name of ingredient | Quantity (mg/g) | Function | Concentration range (mg/g) | Replacement |
|---|---|---|---|---|
| Sodium citrate | 2.7 | pH regulating agent | 1-10 | hydrochloric acid, phosphoric acid, sodium hydroxide, citrate buffer, phosphate buffer, phthalate buffers, acetate buffers, succinate buffers |
| Citric acid, monohydrate | 2.5 | pH regulating agent | | |
| Water, purified | Ad 1 g | Solvent | — | — |

Description of Manufacturing Process

Mometasone furoate is dispersed in a small portion of a propylene glycol and water mixture. The remaining parts of propylene glycol and water are mixed and heated to about 65° C. together with sodium citrate and citric acid. Thereafter, the dispersion of mometasone furoate is added to the aqueous phase.

The ingredients of the oil phase (coconut oil, stearic acid, cetostearyl alcohol, macrogol stearate) are mixed and heated to about 70° C.

The oil phase is added to the aqueous phase. The emulsion is mixed and homogenized and thereafter the cream is cooled during stirring.

DETAILED DESCRIPTION OF MANUFACTURING PROCESS

1. Mometasone furoate dispersion.
   Mix a small, suitable amount of 2 parts purified water and 1 part propylene glycol in a vessel. Add mometasone furoate to the vessel. Stir the mixture for 5 minutes, until the active substance is dispersed.
2. Mixing and heating of water phase to clear solution.
   Add sodium citrate, citric acid monohydrate, propylene glycol and purified water to a vessel. Heat to 65° C.±5° C. during mixing at low speed. Control that a clear solution is obtained.
3. Addition of the mometasone furoate dispersion to the water phase.
   Add the dispersed active substance to the water phase.
4. Add raw material to oil phase.
   Add all the raw materials of the oil phase to a vessel.
5. Melting and heating of oil phase
   Heat and melt the oil phase to 70° C.±5° C.
6. Mixing to homogeneous solution.
   Control that the oil phase is a homogeneous solution.
7. Transfer the oil phase to the water phase.
   Transfer all the oil phase to the water phase.
8. Mixing.
   Mix the two phases until a white emulsion has emerged. Use medium mixing speed.
9. Add vacuum.
   Carefully add vacuum.
10. Homogenisation.
    Homogenize the emulsion for about 5-10 minutes, while stirring.
11. Cooling.
    Cool the emulsion while stirring, until the temperature of the emulsion reaches 25° C.
12. Final mixing.
    When the cream (emulsion) has reached a temperature of 25° C., mix for additional 15 minutes at low speed.

Stability Data

After storage at 25° C./60% RH and 40° C./75% RH for up to 9 months, the 0.1% mometasone furoate oil-in-water cream is stable both chemically and physically, see table 2 and 3.

Samples with the composition according to table 1 but with 20% (w/w) propylene glycol have been stored at 25° C./60% RH and 40° C./75% RH. Stability data is available for up to 12 months, see table 4 and 5. Data shows that the composition is stable at both temperatures for the investigated period.

TABLE 2

Stability data after storage of the composition according to table 1, Mometasone furoate 0.1% cream, batch No. 90016-0806-07, at 25° C./60% RH in aluminum laminated co-extruded PE 100 g tubes.

| | | | | Related substances | | | |
|---|---|---|---|---|---|---|---|
| Storage Months | Appearance | pH | Assay, mometasone furoate % (m/m) | Unknown RRT = 0.77 area-% | Unknown RRT = 1.03 area-% | Unknown RRT = 1.07 area-% | Sum of related substances area-% |
| 0 | Complies | 4.7 | 0.098 | <0.10 | <0.10 | 0.10 | 0.10 |
| 3 | Complies | 4.5 | 0.098 | <0.10 | <0.10 | 0.11 | 0.11 |
| 6 | Complies | 4.6 | 0.099 | <0.10 | <0.10 | 0.11 | 0.11 |
| 9 | Complies | 4.6 | 0.099 | <0.10 | <0.10 | 0.11 | 0.11 |

TABLE 3

Stability data after storage of the composition according to table 1, Mometasone furoate 0.1% cream, batch No. 90016-0806-07, at 40° C./75% RH in aluminum laminated co-extruded PE 100 g tubes.

| Storage Months | Appearance | pH | Assay, mometasone furoate % (m/m) | Related substances | | | |
|---|---|---|---|---|---|---|---|
| | | | | Unknown RRT = 0.77 area-% | Unknown RRT = 1.03 area-% | Unknown RRT = 1.07 area-% | Sum of related substances area-% |
| 0 | Complies | 4.7 | 0.098 | <0.10 | <0.10 | 0.10 | 0.10 |
| 3 | Complies | 4.5 | 0.097 | <0.10 | 0.12 | 0.10 | 0.22 |
| 6 | Complies | 4.5 | 0.098 | <0.10 | 0.18 | 0.10 | 0.28 |

TABLE 4

Stability data after storage of the composition according to table 1 but with 20% (w/w) propylene glycol, Mometasone furoate 0.1% cream, batch No. 90016-0712-14, at 25° C./60% RH in 30 g aluminum tubes.

| Storage Months | Appearance | pH | Assay, mometasone furoate % (m/m) | Related substances | | | |
|---|---|---|---|---|---|---|---|
| | | | | Unknown RRT = 0.77 area-% | Unknown RRT = 1.03 area-% | Unknown RRT = 1.07 area-% | Sum of related substances area-% |
| 0 | Complies | 4.6 | 0.100 | <0.10 | <0.10 | <0.10 | <0.10 |
| 1 | n.a. | n.a. | n.a. | n.a. | n.a. | n.a. | n.a. |
| 4 | Complies | 4.6 | 0.103 | <0.10 | <0.10 | <0.10 | <0.10 |
| 6 | Complies | 4.8 | 0.100 | <0.10 | <0.10 | 0.10 | 0.10 |
| 12 | Complies | 4.6 | 0.102 | <0.10 | <0.10 | 0.11 | 0.11 | n.a. = not analysed

TABLE 5

Stability data of the composition according to table 1 but with 20% (w/w) propylene glycol, Mometasone furoate 0.1% cream, batch No. 90016-0712-14, after storage at 40° C./75% RH in 30 g aluminum tubes.

| Storage Months | Appearance | pH | Assay, mometasone furoate % (m/m) | Related substances | | | |
|---|---|---|---|---|---|---|---|
| | | | | Unknown RRT = 0.77 area-% | Unknown RRT = 1.03 area-% | Unknown RRT = 1.07 area-% | Sum of related substances area-% |
| 0 | Complies | 4.6 | 0.100 | <0.10 | <0.10 | <0.10 | <0.10 |
| 1 | Complies | 4.7 | 0.101 | <0.10 | <0.10 | <0.10 | <0.10 |
| 3 | Complies | 4.7 | 0.105 | <0.10 | <0.10 | <0.10 | <0.10 |
| 6 | Complies | 4.8 | 0.100 | <0.10 | 0.16 | 0.10 | 0.26 |

Example 2

In vivo Behavior of the Oil-In-Water Emulsion of Example 1

VCA Screening Study

Figure 1:
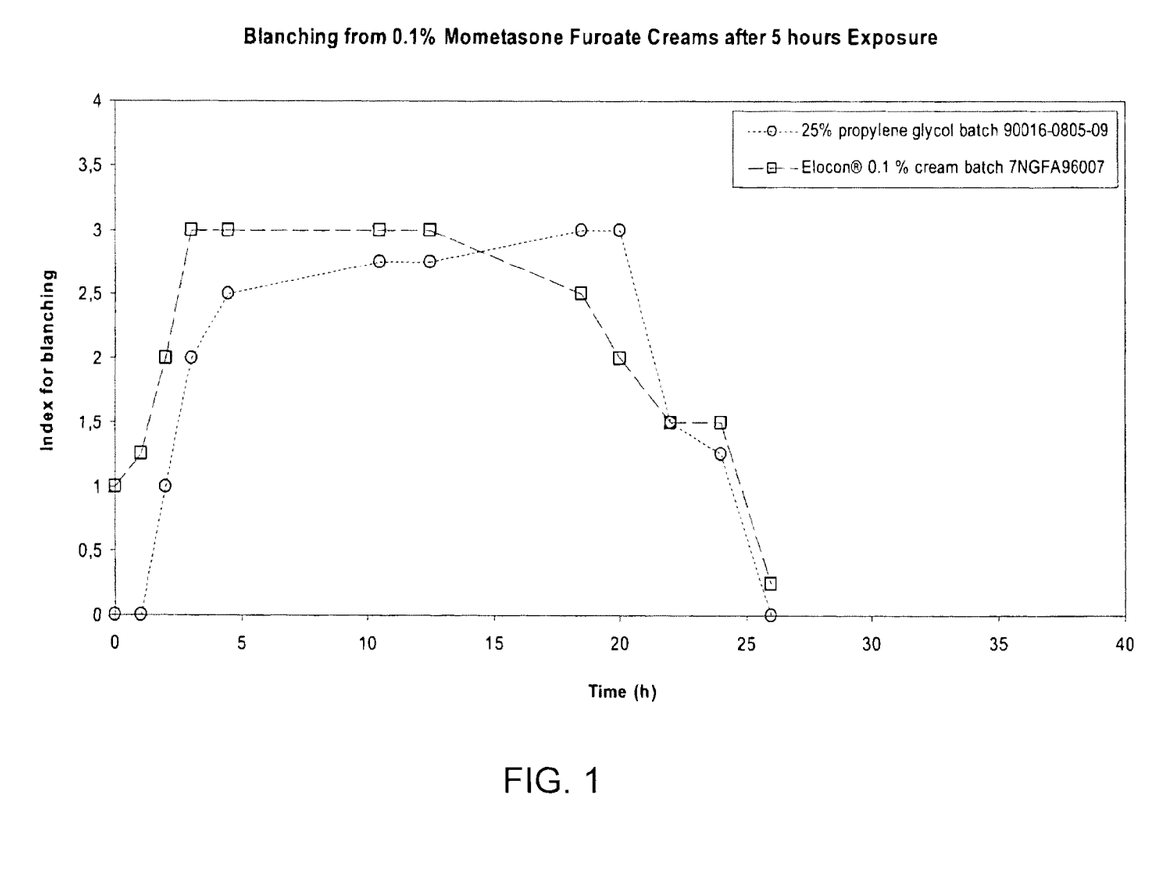
FIG. 1 shows skin blanching as a function of time for the oil-in-water cream with a composition given in Example 1, containing 25% propylene glycol, and the commercial water-in-oil cream Elocon® 0.1% cream. The skin is exposed to the creams 5 hours prior to evaluation (results from Example 2).

Skin blanching has been evaluated to assess the topical bioavailability of the 0.1% mometasone furoate oil-in-water cream given in Example 1, see FIG. 1. The blanching effect has been compared to Elocon® 0.1% cream. Elocon® 0.1% cream is a water-in-oil emulsion, containing 0.1% mometasone furoate. In FIG. 1, it can be seen that the skin blanching and thereby the bioavailability of the 0.1% mometasone furoate oil-in-water cream is comparable to that of Elocon® 0.1% cream.

Figure 2:
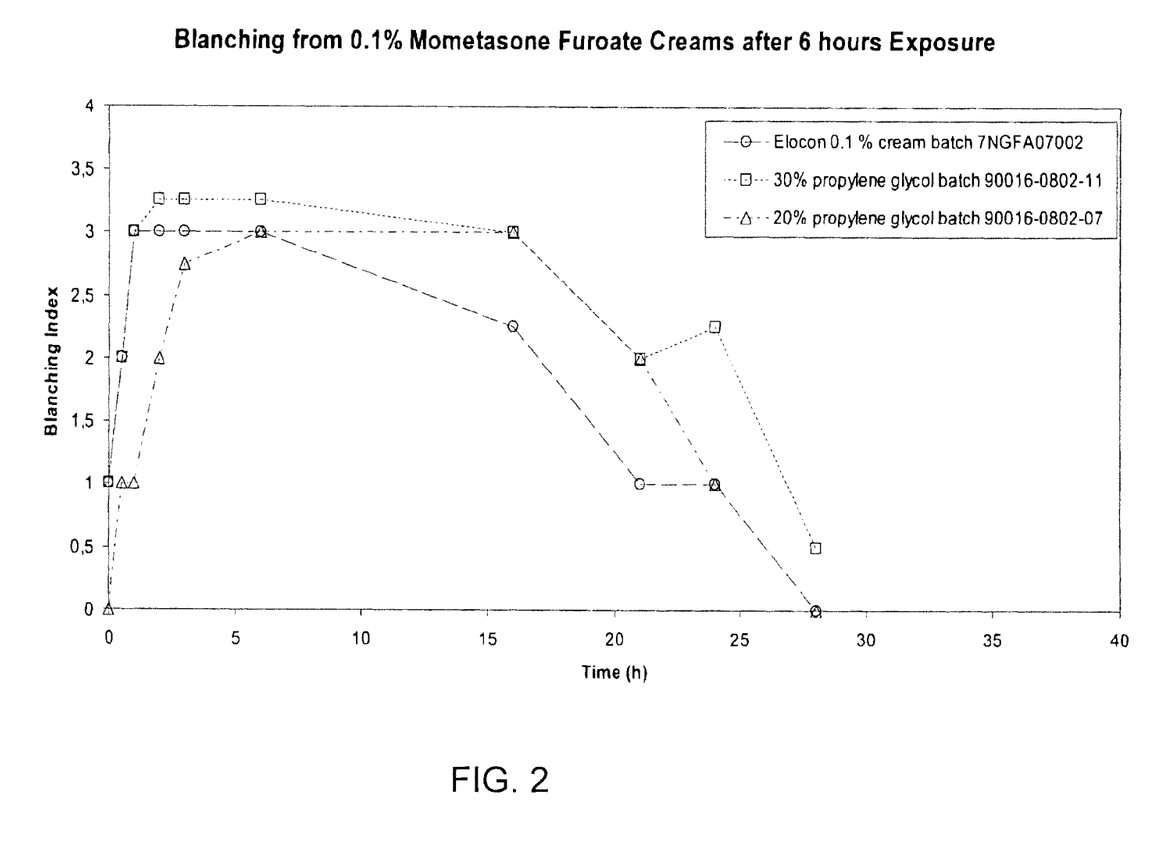
FIG. 2 shows skin blanching as a function of time for oil-in-water creams, containing 20% (PG:W of 1:2.8) and 30% (PG:W of 1:1.5) propylene glycol, and the commercial water-in-oil cream Elocon® 0.1% cream. The skin is exposed to the creams 6 hours prior to evaluation (results from Example 2).

In FIG. 2, skin blanching after applying 0.1% mometasone furoate oil-in-water creams containing 20% and 30% propylene glycol was compared with Elocon® 0.1% cream. Also for these creams the skin blanching was comparable to that of Elocon® 0.1% cream. The creams employed has a PG:W ratio of from 1:1.5 to 1:2.8.

Figure 3:
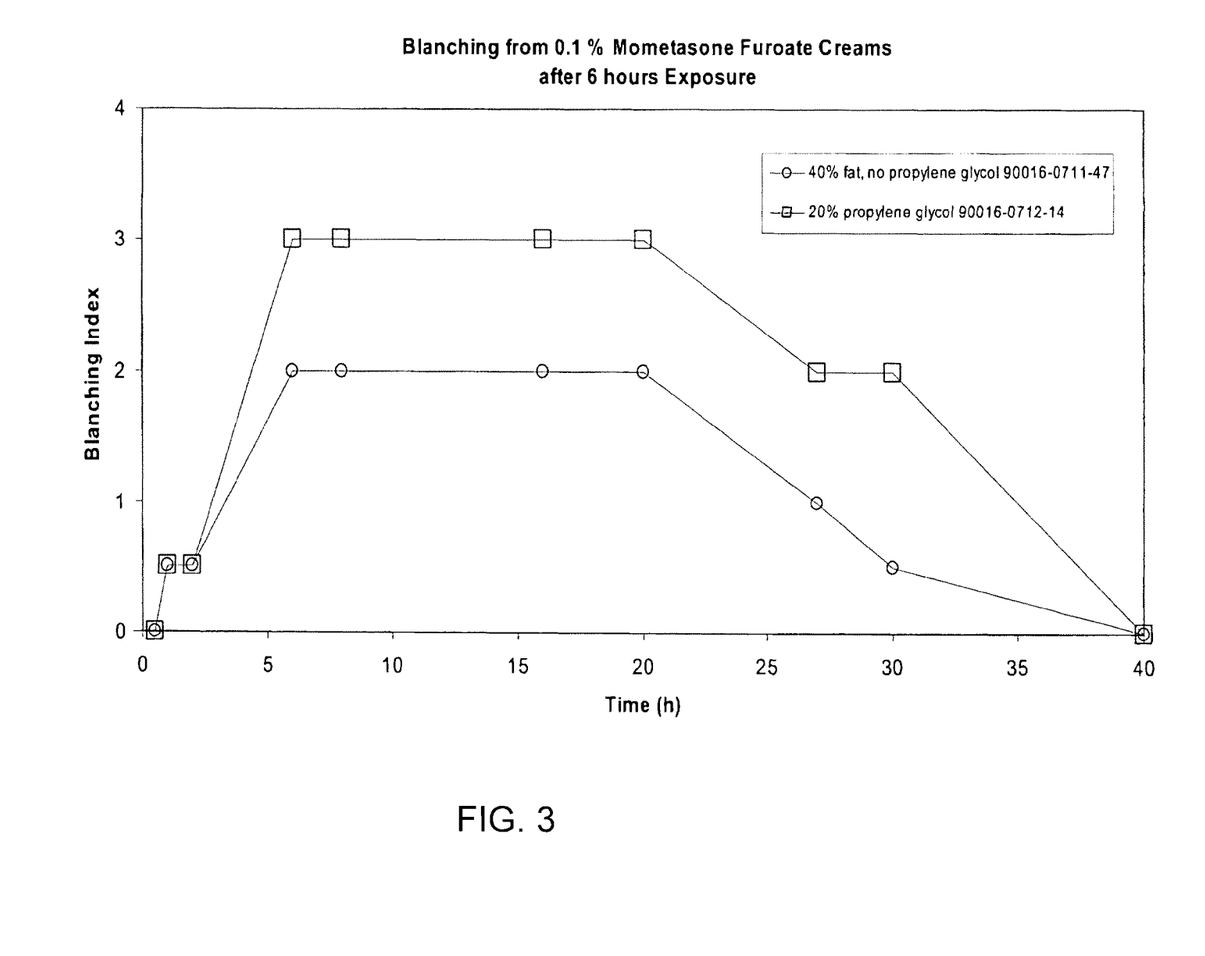
FIG. 3 shows skin blanching as a function of time for oil-in-water creams containing 20% oil/fat mainly coconut oil (includes all ingredients with HLB≤11) and 20% propylene glycol (90016-0712-14); 40% oil/fat mainly paraffin oil and white soft paraffin (includes all ingredients with HLB≤11) and no propylene glycol (90016-0711-47). The skin is exposed to the creams 6 hours prior to evaluation (results from Example 2).

The effect on skin blanching after applying an oil-in-water cream with a high fat content (40%) and no propylene glycol was compared with the effect of a cream with 20% propylene glycol and 20% fat, see FIG. 3. It can be seen that the presence of propylene glycol in the formulations is more important than a high fat content.

In the in-vivo screening studies, approximately 40 mg of each cream was applied to a 2.25 cm$^2$ test field located on the volar part of the forearm. The non-occlusive application was removed after 5 hours (FIG. 1) or 6 hours (FIGS. 2 and 3) exposure of the creams. Prior to the creams were applied, the skin color was determined by comparing the color of the test field with shades in a color atlas (Natural Color System SS019102, 2$^{nd}$ ed.). White is given an index of 4 (color 0502-Y) and untreated skin color on this object gave an index of 0 (color S10-C20-Y5OR).

VCA Study

Figure 4:
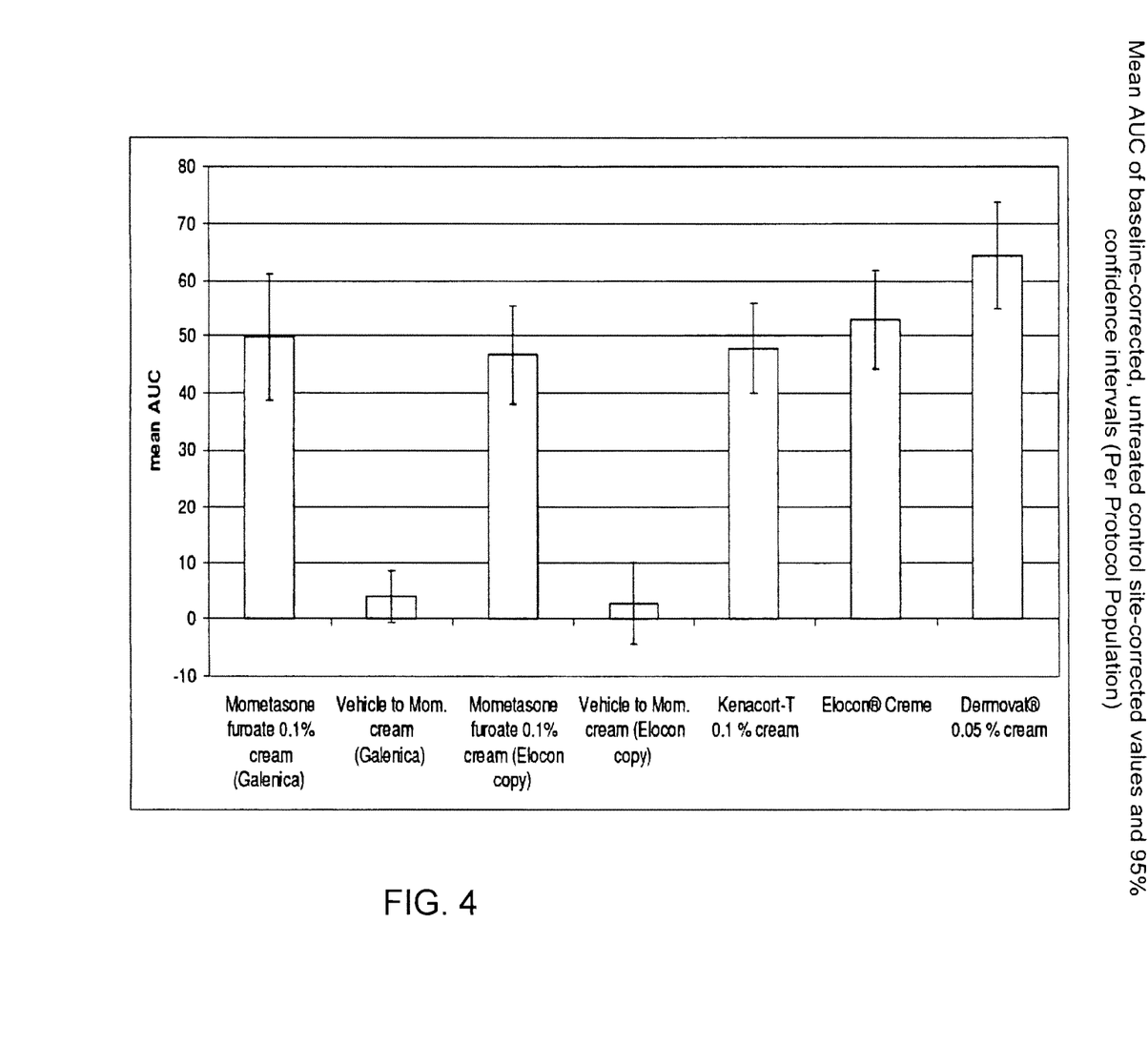
FIG. 4. Mean AUC of baseline-corrected, untreated control site-corrected values and 95% confidence intervals (Per Protocol Population)—results from Example 2.
Figure 5:
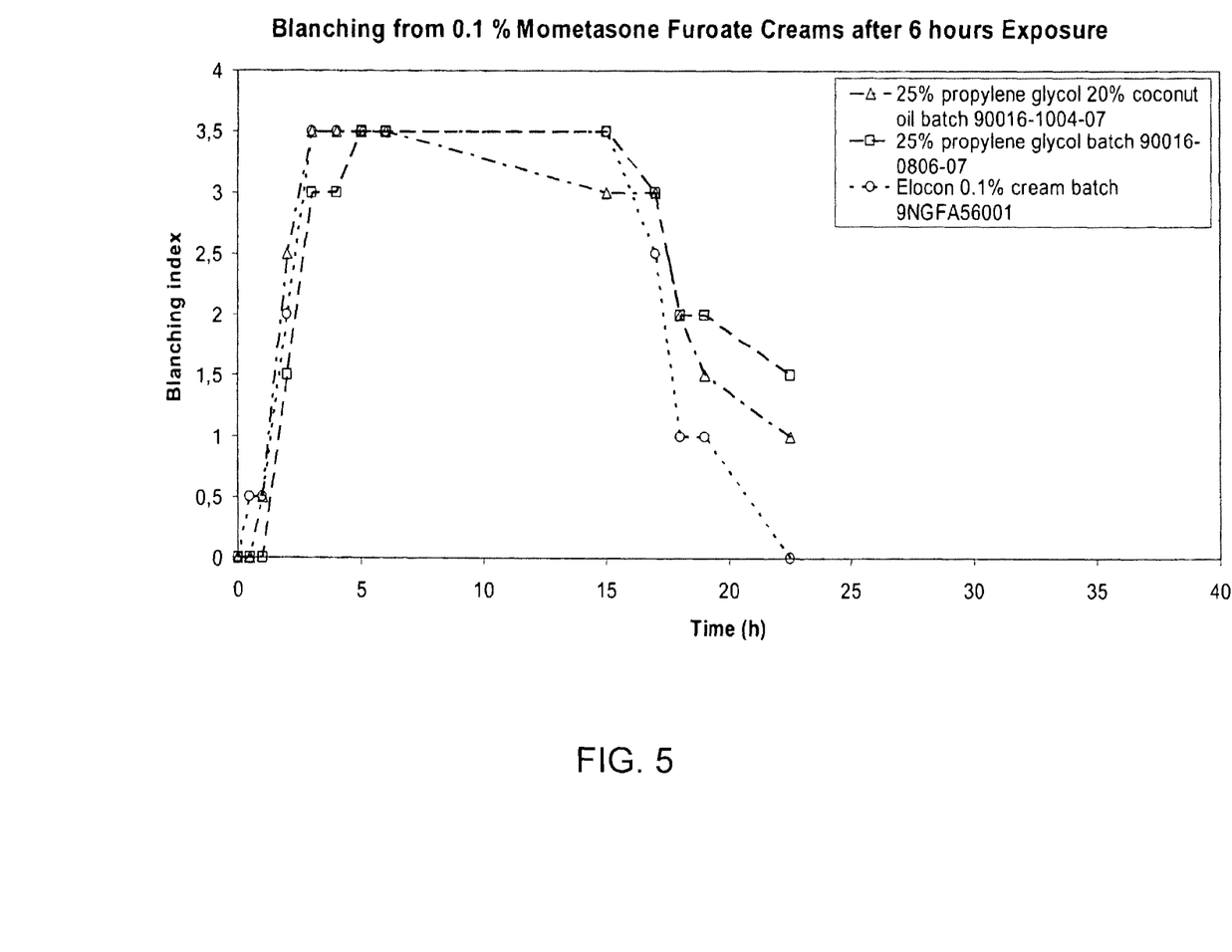
FIG. 5 shows skin blanching as a function of time for oil-in-water creams containing i) 25% propylene glycol and 20% coconut oil (weight ratio PG:W of 1:1.58) and ii) the composition described in table 1 herein (PG:W of 1:2.06), and the commercial water-in-oil cream Elocon® 0.1% cream. The skin is exposed to the creams 6 hours prior to evaluation—results from Example 3.

A vasoconstrictor assay (VCA) study on 30 healthy subjects, vehicle controlled single-center double blind study for the study preparations (Mometasone furorate 0.1% cream, Galenica (the invention) and Elocon generic copy, class III) observer-blind for the comparators (Kenacort-T 0.1% cream, Elocon® 0.1% cream and Dermovat 0.05% cream, class II, III and IV respectively) was performed. Approximately 50 µl cream was applied to a total of nine test fields of 2 cm$^2$ each, located on the volar surface of the forearms, non-occlusive for 6 hours. The skin color was measured prior to treatment (baseline) and after 1, 2, 4, 6, 18 and 24 hours after the end of the treatment period with a Minolta Chroma-Meter CR-300. The total mean skin blanching was assessed as baseline corrected AUC for the tested creams according to FIG. 4.

The result shows that topical bioequivalence is possible to obtain with the described o/w cream when compared to the Elocon® w/o cream.

Antimicrobial Properties

The 0.1% mometasone furoate oil-in-water cream has been challenge tested according to Ph. Eur. "Efficacy of Antimicrobial Preservation". The o/w cream showed that the formulation satisfies criteria in Ph. Eur. 5.1.3. Hence, the product is self preserved and has antimicrobial properties.

Example 3

In vivo Behavior of the Oil-in-Water Emulsions of the Invention

Two compositions of the present invention and Elocon® 0.1% were tested as described in Example 2 above. The compositions of the invention had different weight ratios PG:W, namely from 1:1.6 to 1:2.1. The composition with the weight ratio 1:1.6 was in accordance with the composition described in Table 1 herein, but contained 20% w/w coconut; the content of water was reduced accordingly. The composition with the weight ratio 1:2.1 contained 25% propylene glycol and had a composition as described in Table 1 herein.

The results show that both compositions have therapeutic effects similar to that of Elocon® cream.

Example 4

Comparison of in vivo Behaviour of an Oil-in-Water Emulsion According to the Present Invention with Formulations According to WO 2008/126076 (Perrigo Israel Pharmaceuticals Ltd)

As mentioned in the introduction herein, an oil-in-water composition of mometasone has been described in WO 2008/126076. However, no in vivo studies have been reported. In order to compare the in vivo behaviour of compositions according to the present invention with those of WO 2008/126076 (denoted Perrigo creams), a comparison study was made.

The compositions described in Example 3 (Formula B) and Example 5 (Formula C) were prepared as follows:

Composition Perrigo Mometasone furoate 0.1% cream (comparative cream according to WO 2008/126076)

| Formula B (Comparative) in patent WO2008/126076 | |
|---|---|
| Ingredients | Concentration (wt %) |
| Mometasone furoate | 0.1 |
| Phosphoric acid | 0.525 |
| Purified water | 53.7 |
| Xanthan gum | 0.2 |
| Carbomer 940 | 0.3 |
| Dibasic sodium phosphate anhydrous (corresponding to 1.0 wt % heptahydrate) | 0.53 |
| Emulsifying wax (Polawax) | 8.0 |
| Benzyl alcohol | 1.0 |
| Propylene glycol | 15.0 |
| Cetostearyl alcohol | 7.0 |
| Oleic acid | 1.2 |
| Caprylic capric triglyceride | 12.0 |

| Formula C (Invention) in patent WO2008/126076 | |
|---|---|
| Ingredients | Concentration (wt %) |
| Mometasone furoate | 0.075 |
| Xanthan gum | 0.2 |
| Carbomer 940 | 0.3 |
| Dibasic sodium phosphate anhydrous (corresponding to 1.0 wt % heptahydrate) | 0.53 |
| Emulsifying wax (Polawax) | 8.0 |
| Benzyl alcohol | 1.0 |
| Propylene glycol | 15.0 |
| Cetostearyl alcohol | 7.0 |
| Oleic acid | 1.2 |
| Caprylic capric triglyceride | 12.0 |
| Phosphoric acid | 0.525 |
| Purified water | 53.7 |

Preparation of Creams:

The water phase is prepared first: Xanthan gum and carbomer 940 are dispersed in purified water. Next dibasic sodium phosphate is mixed into the dispersion. Emulsifying wax and benzyl alcohol are added to the dispersion and heated.

To prepare the active solution, mometasone furoate is dissolved in heated propylene glycol.

Next the oily phase is prepared: Oleic acid, cetostearyl alcohol, and caprylic capric triglyceride are combined and mixed.

The active solution and the oily phase are added to the water phase.

The resulting emulsion is cooled. pH is adjusted with phosphoric acid.

Figure 6:
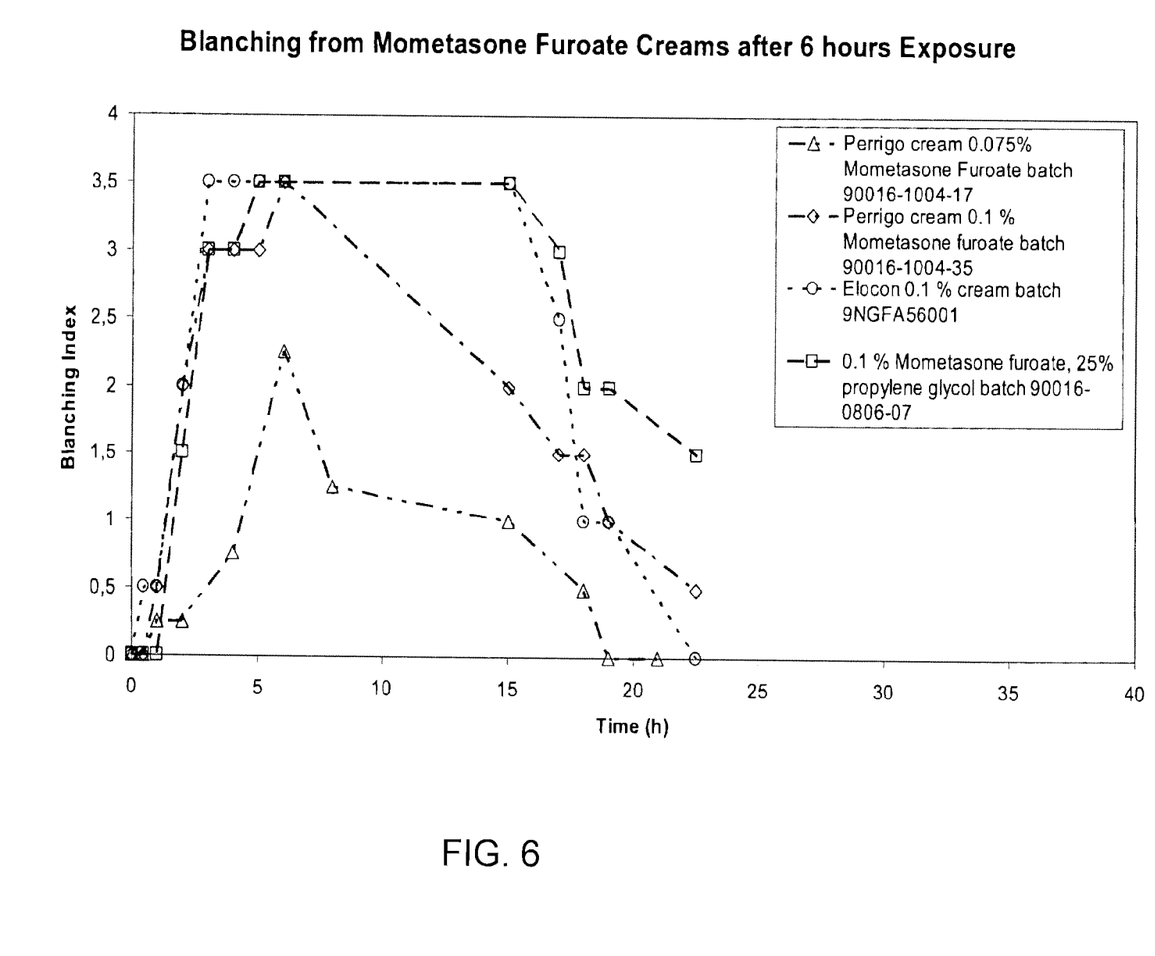
FIG. 6 shows skin blanching as a function of time for a cream according to the invention compared with Elocon® 0.1% cream and creams prepared according to examples 3 and 5, respectively, of WO 2008/126076 (in short: Perrigo creams). PG:W of Perrigo creams is 1:3.6.

The Perrigo compositions and a composition according to the present invention and Elocon® 0.1% cream were subjected to the skin blanching study described in Example 2 above and the results are reported in FIG. 6. The results clearly demonstrate that the Perrigo creams do not lead to similar therapeutic effect as the Elocon® cream, whereas a composition of the invention has similar therapeutic effect as Elocon® cream.

The invention claimed is:

1. An oil-in-water emulsion topical mometasone pharmaceutical composition formulated for application to skin, comprising
from 0.075% to 0.2% mometasone furoate;
from about 20 to about 45% w/w of propylene glycol;
from 5-15% w/w of coconut oil;
from 1-15% w/w of one or more emulsifying agents selected from glycerol alkyl esters, macrogol alkyl esters, polyoxyethyleneglycol alkyl esters, fatty acids, polyoxyethylene sorbitan esters, polyoxyethylene alkyl ethers, and galactolipids; and water, wherein the w/w amounts are based on the total weight of the emulsion;

wherein the emulsion comprises undissolved mometasone furoate in micronized form, wherein the micronized mometasone furoate has a particle size distribution such that 100% of the particles have a particle size <20 µm, 99% have a particle size <15 µm, and 80% have a particle size <5 µm; and, wherein, after topical application, the emulsion achieves an area under the curve (AUC) of blanching index as a function of time that is at least 85% of that achieved by ELOCON° cream 0.1%, which is a water-in-oil emulsion which contains mometasone furoate USP in an amount of 1 mg/g of cream in a cream base comprising hexylene glycol NF, in an amount of 120 mg/g of cream, propylene glycol stearate having a monoester content of 55% in an amount of 80 mg/g of cream, ceteareth-20 compounded with stearyl alcohol in an amount of 70 mg/g of cream, titanium dioxide USP in an amount of 10 mg/g of cream, gamma-irradiated aluminium starch octenylsuccinate in an amount of 100 mg/g of cream, white wax NF in an amount of 50 mg/g of cream, white petrolatum USP in an amount of 539 mg/g of cream, purified water USP in an amount of 30 mg/g of cream, and phosphoric acid NF in an amount used to adjust the pH of the purified water to pH 2.5±0.2 charged as a 10% w/v solution.

2. The oil-in-water emulsion according to claim 1, wherein the concentration of propylene glycol is from about 20 to about 40% w/w based on the total weight of the emulsion.

3. The oil-in-water emulsion according to claim 1, wherein the concentration of propylene glycol is from about 20 to about 30% w/w based on the total weight of the emulsion.

4. The oil-in-water emulsion according to claim 1, wherein the weight ratio of propylene glycol to water in the oil-in-water emulsion is from about 1:1.5 to about 1:2.5.

5. The oil-in-water emulsion according to claim 1, wherein the mometasone furoate is the sole therapeutically active ingredient.

6. The oil-in-water emulsion according to claim 1, wherein from about 25% to about 35% w/w of the total amount of the mometasone furoate in the emulsion is present in undissolved form.

7. The oil-in-water emulsion according to claim 1, wherein the oil further comprises an oil selected from animal oils, mineral oils, ester oils, and silicon oils.

8. The oil-in-water emulsion according to claim 1, wherein the oil-in-water emulsion comprises more than one emulsifying agent.

9. The oil-in-water emulsion according to claim 8, comprising one or more emulsifying agents having a hydrophilic-lipophilic balance (HLB) in the range of 3-20.

10. The oil-in-water emulsion according to claim 9, comprising one or more emulsifying agents with a HLB of from about 11 to about 20.

11. The oil-in-water emulsion according to claim 9, comprising one or more emulsifying agents with a HLB of from about 3 to about 11.

12. The oil-in-water emulsion according to claim 8, wherein the emulsifying agents are selected from glycerol monostearate 40-55, macrogol stearate, and stearic acid.

13. The oil-in-water emulsion according to claim 8, wherein the concentration of each emulsifier in the emulsion ranges from 1-5% w/w based on the total weight of the emulsion.

14. The oil-in-water emulsion according to claim 1, further comprising a viscosity-increasing agent.

15. The oil-in-water emulsion according to claim 4, wherein the viscosity-increasing agent is a fatty alcohol.

16. The oil-in-water emulsion according to claim 14, wherein the viscosity-increasing agent is cetostearyl alcohol.

17. The oil-in-water emulsion according to claim 1, wherein the emulsion further comprises 0.1-1% w/w of a pH adjusting agent and 5-15% w/w viscosity increasing agent, all based on the total weight of the emulsion.

18. The oil-in-water emulsion of claim 1, containing about 0.1% w/w of mometasone furoate.

19. The oil-in-water emulsion according to claim 1, wherein the emulsion does not contain N-methyl-2-pyrrolidone.

20. The oil-in-water emulsion according to claim 1, wherein the emulsion does not contain any preservative other than propylene glycol.

21. The oil-in-water emulsion of claim 1, wherein the emulsion is physically and chemically stable for a period of 6 months at 40° C/75% RH.

22. The oil-in-water emulsion of claim 1, wherein the emulsion is physically and chemically stable for a period of 9 to 12 months at 25° C/60% RH.

\* \* \* \* \*